(12) United States Patent
Kowarschik et al.

(10) Patent No.: US 10,524,755 B2
(45) Date of Patent: Jan. 7, 2020

(54) METHOD, IMAGE PROCESSING DEVICE, COMPUTER PROGRAM AND ELECTRONICALLY READABLE DATA CARRIER FOR REDUCING VESSEL OVERLAP ARTIFACTS IN A FOUR-DIMENSIONAL ANGIOGRAPHY DATA SET

(71) Applicants: Markus Kowarschik, Nürnberg (DE); Christopher Rohkohl, Brixen im Thale (DE); Sonja Gehrisch, Nürnberg (DE)

(72) Inventors: Markus Kowarschik, Nürnberg (DE); Christopher Rohkohl, Brixen im Thale (DE); Sonja Gehrisch, Nürnberg (DE)

(73) Assignee: Siemens Healthcare GmbH, Erlangen (DE)

( * ) Notice: Subject to any disclaimer, the term of this patent is extended or adjusted under 35 U.S.C. 154(b) by 158 days.

(21) Appl. No.: 15/866,962

(22) Filed: Jan. 10, 2018

(65) Prior Publication Data

US 2018/0199905 A1 Jul. 19, 2018

(30) Foreign Application Priority Data

Jan. 13, 2017 (DE) .................. 10 2017 200 489

(51) Int. Cl.
*G06K 9/00* (2006.01)
*A61B 5/00* (2006.01)
(Continued)

(52) U.S. Cl.
CPC .......... *A61B 6/5217* (2013.01); *A61B 6/4441* (2013.01); *A61B 6/481* (2013.01);
(Continued)

(58) Field of Classification Search
USPC ....... 382/100, 103, 128–134, 154, 162, 168, 382/173, 181, 199, 219, 224, 232, 254,
(Continued)

(56) References Cited

U.S. PATENT DOCUMENTS 9,443,330 B2* 9/2016 Heigl .................... G06T 11/008
2015/0335304 A1* 11/2015 Lavi ...................... G06F 19/321
600/407

(Continued)

OTHER PUBLICATIONS

Davis, Brian et al.: "4D Digital Subtraction Angiography: Implementation and Demonstration of Feasibility"; in: American Society of Neuroradiology, 2013, vol. 34, pp. 1-8, http://dx.doi.org/10.3174/ajnr.A3529.

(Continued)

*Primary Examiner* — Seyed H Azarian
(74) *Attorney, Agent, or Firm* — Lempia Summerfield Katz LLC

(57) ABSTRACT

Vessel overlap artifacts are reduced in a four-dimensional angiography data set a blood vessel system of a patient with a contrast medium. A three-dimensional vessel data set of the blood vessel system is reconstructed from two-dimensional projection images of digital subtraction angiography showing the blood vessel system, determined by multiplicative back projection of the projection images into the vessel data set or a base data set of the four-dimensional angiography data set derived vessel data set. A plausibility check is performed with vessel sections displayed as filled with contrast medium in partial image data sets of the angiography data set assigned to all individual, and different instants of the covered period are checked against a plausibility check criterion checking for a contrast medium-filled connection to an admissible source point, after which a corrected partial image data set is determined containing
(Continued)

only vessel sections satisfying the plausibility check criterion.

14 Claims, 3 Drawing Sheets

(51) Int. Cl.
    *A61B 6/00*     (2006.01)
    *G06T 5/50*     (2006.01)

(52) U.S. Cl.
    CPC ............... *A61B 6/504* (2013.01); *G06T 5/50* (2013.01); *G06T 2207/10116* (2013.01); *G06T 2207/30101* (2013.01)

(58) Field of Classification Search
    USPC ...... 382/274–276, 285, 291, 305; 378/4, 21, 378/98.12; 600/407, 324
    See application file for complete search history.

(56) References Cited

U.S. PATENT DOCUMENTS

| | | | |
|---|---|---|---|
| 2015/0339847 A1* | 11/2015 | Benishti | G16H 50/30 382/131 |
| 2016/0151033 A1* | 6/2016 | Ohishi | A61B 6/5217 378/98.12 |
| 2016/0350948 A1* | 12/2016 | Heigl | G06T 11/008 |
| 2017/0249758 A1* | 8/2017 | Mistretta | A61B 6/025 |

OTHER PUBLICATIONS

German Office Action for related German Application No. 10 2017 200 489.4 dated Sep. 18, 2017.

* cited by examiner

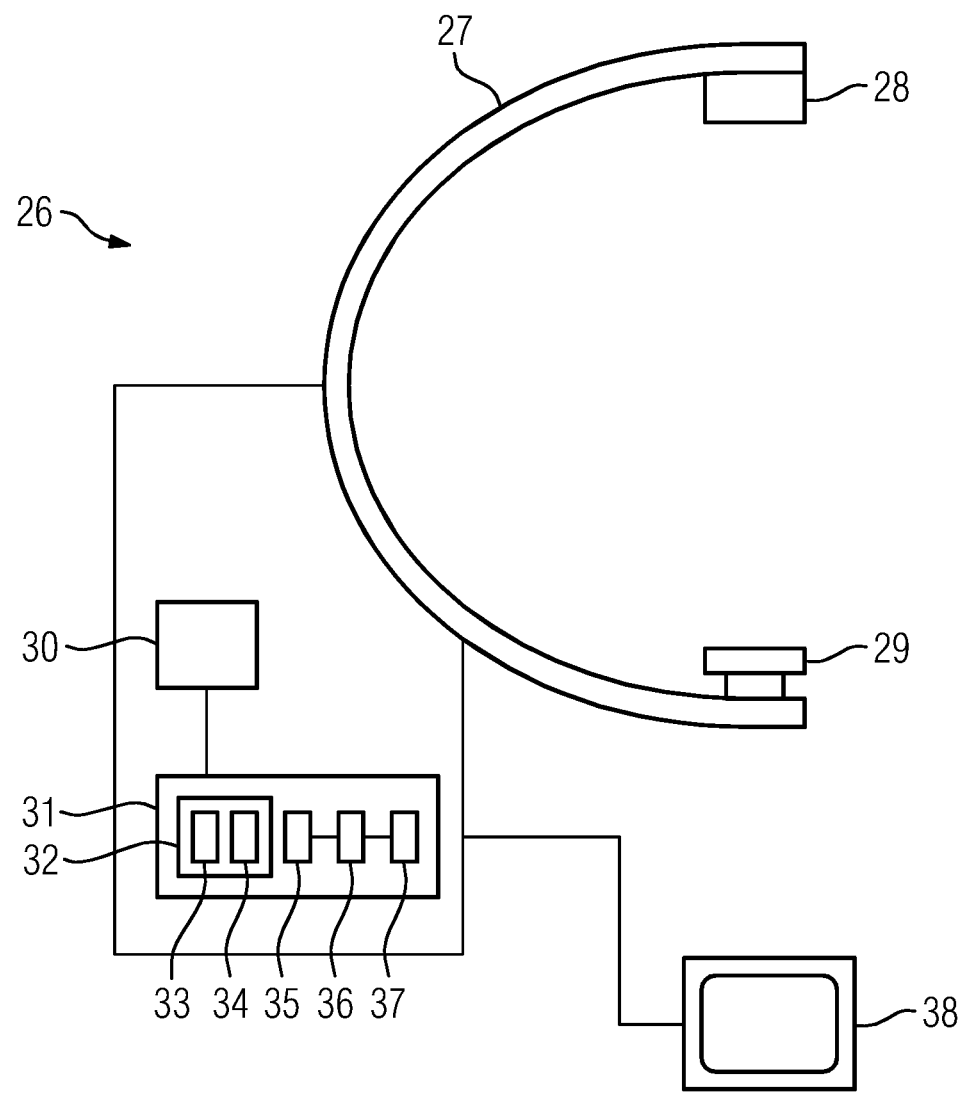

METHOD, IMAGE PROCESSING DEVICE, COMPUTER PROGRAM AND ELECTRONICALLY READABLE DATA CARRIER FOR REDUCING VESSEL OVERLAP ARTIFACTS IN A FOUR-DIMENSIONAL ANGIOGRAPHY DATA SET

CROSS-REFERENCE TO RELATED APPLICATIONS

The present patent document claims the benefit of DE 102017200489.4, filed on Jan. 13, 2017, which is hereby incorporated by reference in its entirety.

BACKGROUND

Overlapping vessels are a fundamentally known problem in digital subtraction angiography (DSA). A large move in the direction of reliable images that can be effectively interpreted was the development of four-dimensional digital subtraction angiography. In four-dimensional digital subtraction angiography, two-dimensional projection images of the recording region of interest of the blood vessel system of the patient are recorded using X-ray equipment (e.g., X-ray equipment having a C-arm, with one or more rotation(s) at different projection angles) while the contrast medium migrates through the blood vessel system in the recording region. Projection images of digital subtraction angiography are produced subtracting a mask image recorded without contrast medium, and a subtraction may also be made for respective reconstructed three-dimensional image data sets. While in the beginnings of digital subtraction angiography it was known to generate a plurality of consecutive three-dimensional image data sets by using projection images from digital subtraction angiography recorded in a particular time interval to reconstruct a three-dimensional partial image data set therefrom, new approaches exist that may provide better image quality and a better temporal resolution.

One of the new approaches is described in an article by B. Davis et al., "4D Digital Subtraction Angiography: Implementation and Demonstration of Feasibility", DOI: 10.3174/ajnr.A3529. It is proposed to firstly reconstruct a non-time resolved, three-dimensional vessel data set showing the entire blood vessel system in the recording region, using a particularly large portion of the projection images from digital subtraction angiography. The projection images exhibit at least largely filled vessels, and the data set forms the basis for continuously updating of the voxel values by multiplicative embedding of the time information of the (e.g., standardized) projection images from digital subtraction angiography, such that a series of time-resolved 3D images (e.g., of partial image data sets of the four-dimensional angiography data set) is produced. In other words, the vessel data set is ultimately used for limiting the reconstruction of the individual three-dimensional partial image data sets which integrate the time information of the projection images from digital subtraction angiography. A multiplicative back projection is therefore performed. This may be taken to mean that vessels (e.g., voxels marked as vessels) located on the beam of a pixel of a projection image, showing contrast medium filling, are highlighted as being contrast medium-filled at the instant of recording of the projection image.

The use of recordings in a single plane and the multiplicative back projection in the four-dimensional image reconstruction may lead to problems when a vessel overlap exists along the beams of the current projection image. More precisely, the multiplicative back projection of a two-dimensional projection image in a static three-dimensional limitation image (e.g., the vessel data set, without additional regularization) leads to non-plausible vessel highlighting because the contrast information of the two-dimensional projection image may not be unequivocally assigned to one of the overlapping vessels. Therefore, an algorithm of this kind may create artifacts due to vessel overlapping in that particular vessel segments, displayed too early or too late as being filled with contrast medium. For the user (e.g., a doctor making a diagnosis), the image quality and the clinical significance of this four-dimensional are adversely affected.

To reduce the number of overlap artifacts, it has already been proposed, during multiplicative back projection for determining the three-dimensional partial image data sets assigned to different instants, to simultaneously determine a likewise four-dimensional confidence map as a confidence data set describing the vessel overlap along relevant, used beams. The confidence value 0 is conventionally assigned to a strong vessel overlap and a confidence value 1 is conventionally assigned to a non-existent vessel overlap. Confidence values of the confidence data set may be determined by "counting" the vessels (e.g., by integration along the beam and comparison with at least one threshold value). Based on the four-dimensional confidence data set describing the vessel overlap, it is possible to interpolate unreliable intensity values of the provisional four-dimensional angiography image data set between sufficiently reliable neighboring values in the time and therefore replace the less reliable values (e.g., those falling below a threshold value for the confidence value).

However, it has been found that more potential for improvement exists for this approach with the elimination of the image quality problem due to vessel overlap artifacts.

SUMMARY AND DESCRIPTION

The scope of the present invention is defined solely by the appended claims and is not affected to any degree by the statements within this summary.

One or more of the present embodiments may obviate one or more of the drawbacks or limitations in the related art. For example, reducing vessel overlap artifacts, because of the overlap of vessels, is improved.

The present embodiments relate to a method for reducing vessel overlap artifacts that occur in a four-dimensional angiography data set of a recording region of interest of a blood vessel system of a patient recorded with administration of a contrast medium. A three-dimensional vessel data set of the blood vessel system is reconstructed from two-dimensional projection images of the digital subtraction angiography showing the blood vessel system, determined by multiplicative back projection of the projection images into the vessel data set or a base data set of the four-dimensional angiography data set derived therefrom. The present embodiments also relate to an image processing device, to a computer program and to an electronically readable data carrier.

A method is provided, that in a plausibility check act, vessel sections displayed as filled with contrast medium in partial image data sets of the angiography data set assigned to all individual, different instants of the covered period are checked against a plausibility check criterion checking for the existence of a contrast medium-filled connection to an admissible source point. A corrected partial image data set is determined containing only vessel sections that satisfy the plausibility check criterion.

The four-dimensional angiography data set covers a particular period of the course of the contrast medium concentration in the recording region by way of a time series of three-dimensional partial image data sets. For example, not just one three-dimensional position (voxel) corresponds to each image element of the four-dimensional angiography data set, instead, over the period, each of the image elements includes a contrast medium characteristic curve such that partial image data sets describing contrast medium states corresponding to various instants within the period result from the four-dimensional angiography data set. An instant is a section of the period. For example, an instant, depending on the temporal resolution of the four-dimensional angiography data set, conventionally covers a certain time interval corresponding to the smallest resolvable unit of time or a multiple thereof.

For checking the plausibility of vessel sections displayed as filled with contrast medium, the present embodiments do not start from complex assumptions about the hemodynamics and/or other flow and anatomical properties of the blood vessel system and/or the blood. Instead, the present embodiments consider the individual instants separately and check the plausibility of the connection to admissible source points (e.g., therefore voxels and/or vessel segments may be assumed with a high level of plausibility or reliability to actually be filled with contrast medium). In a plausibility check criterion, a check is made for each vessel section (e.g., displayed as filled with contrast medium) of an instant as to whether a connection (e.g., displayed as filled with contrast medium) to an admissible source point exists. In an example, a check may then be performed when connected components are found in a partial image data set of an instant as to which of these connected components contain an admissible source point as vessel sections (e.g., such that each of their voxels is also connected to the admissible source point filled with contrast medium). The connection to an admissible source point may provide (e.g., as a function of the reliability thereof) that the contrast medium has arrived on a physically possible path at newly highlighted voxels or vessel segments (e.g., those displayed as filled with contrast medium). The present embodiments therefore use physically motivated plausibility check limitations, described by the plausibility check criterion, in order to reduce overlap artifacts in the generated, time-resolved series of volumetric partial image data sets. In this way, perception of the physiological blood flow by an observer is simplified (e.g., even if vessel overlap exists). Vessel sections displayed as filled with contrast medium for which no connection to an admissible source point exists are removed from the partial image data sets or are no longer displayed as filled with contrast medium therein (e.g., because it is physically implausible for the sections to be filled with contrast medium).

A plausibility check-based flow limitation is provided in the four-dimensional reconstruction process using simple physical principles in respect of the flow (e.g., the existence of a flow connection to an admissible source point). Therefore, a reliably filled, displayed voxel or vessel segment reduces the occurrence of incorrect, non-physiological vessel fillings due to vessel overlap. Further, a plausibility check may be inserted in the four-dimensional reconstruction process, providing that a particular vessel segment is only contrast-highlighted when the vessel segment is connected to a voxel or vessel segment and described by the source point, assigned to a reliably contrast medium-filled volume element.

Artifacts of non-physiological vessel section highlighting due to vessel overlap may be reduced and users may assess the blood flow in the vascular tree more accurately because the image quality of the four-dimensional angiography image data set may be significantly increased.

The present embodiments may not use any further hemodynamic properties and/or physical models in respect of reliable flow directions, blood flow speeds, blood properties and the like. In this regard, the present embodiments may use just one plausibility limitation in respect of vessel filling in such a way that (e.g., pathological flow directions, such as the reverse filling of vessels) may occur in patients with vascular disorders (e.g., a stenosis) are admissible.

Admissible source points may be used as voxels located at the edge of the recording region and/or voxels displayed as filled with contrast medium in an immediately preceding partial image data set (e.g., already corrected) and in the current partial image data set. Voxels located at the edge of the recording region are may be expedient when the contrast medium administering device administering the contrast medium is situated outside of the recording region and the contrast medium flows into the recording region from the edge. In other words, it may be assumed in a plausibility-checking manner that the recording region fills from the edge, such that edge points of this kind or edge vessel segments are extremely expedient precisely for initialization. In a case where only the filling of vessels is displayed, voxels marked as being filled with contrast medium remain filled with contrast medium through to the end of the period, and voxels located at the edge of the recording region may be dealt with continuously as admissible source points. However, in cases that are intended to and may display that the contrast medium bolus removes itself from the edge of the recording region and penetrates further into the recording region, voxels displayed as filled with contrast medium may be used as admissible source points in an immediately preceding partial image data set (e.g., already corrected) and in the current partial image data set. In other words, at one instant a new voxel may only be filled with contrast medium if a further voxel existed in the immediately preceding instant (e.g., the corresponding partial image data set displayed as filled with contrast medium and is also connected to the new voxel). This physically motivated plausibility check consideration is mapped by the choice of an admissible source point as voxels displayed as filled with contrast medium in the partial image data set currently being considered and in the immediately preceding one. In this context, the partial image data sets and the connected voxel sections that may be found therein are consecutively analyzed.

It is also conceivable to record four-dimensional angiography data sets if the contrast medium administering device (e.g., an appropriate catheter) is situated inside the recording region of interest. At least for initialization, admissible source points are determined as a position of a contrast medium administering device inside the recording region. In other words, knowledge about where the contrast medium administering device is situated is used to determine source points from which contrast medium filling inevitably starts. Depending on the duration of the bolus administration and/or type of selected display (e.g., as only filling), the admissible source points may remain in force as admissible source points and/or may be supplemented or replaced by corresponding voxels displayed as being filled with contrast medium in the current partial image data set and in the immediately preceding partial image data set.

The present embodiments allow outflow processes to also be displayed in an artifact-reduced manner because, due to the multiplicative back projection, an erroneous "empty display" of a vessel may not occur. Instead, only erroneous contrast medium filling in vessel sections is displayed. However, the plausibility check provides that "detached" vessel sections without an admissible source point may also be found during outflow of the contrast mediums (e.g., when the partial image data sets are processed) and additionally in reverse (e.g., running back in the time from the end of the period). For example, the present embodiments provide that because the contrast medium flows out of the recording region (e.g., at least for initialization), admissible source points located at the edge, and in this case admissible source points that are displayed as filled with contrast medium in the following partial image data set and in the partial image data set currently being considered, are used. In other words, when both an inflow and an outflow of contrast medium from the recording region of interest is to be displayed, at least some of the partial image data sets (e.g., beginning with the start point of the period) may be successively plausibility checked in the time lapse direction and a further portion of the partial image data sets (e.g., starting from the end point of the period) may be plausibility checked counter to the time direction (e.g., in each case up to the instant of maximum contrast medium filling). In this way, physically implausible filling phenomena are diminished or reduced both in the inflow behavior and in the outflow behavior.

As such, the present embodiments provide that with an angiography data set showing the inflow of contrast medium into and the outflow of contrast medium out of the recording region of interest, and using admissible source points as voxels displayed as filled with contrast medium in successive partial image data sets in the period, an inflow interval beginning with the start of the period and an outflow interval ending with the end of the period are defined. In the inflow interval, the partial image data sets are checked in successive order, and admissible source points are determined at least partially as voxels displayed as filled with contrast medium in an immediately preceding partial image data set (e.g., already having been corrected), and in the current partial image data set, and in the outflow interval the partial image data sets are checked in the reverse chronological order. Admissible source points are determined at least partially as voxels displayed as filled with contrast medium in an immediately following partial image data set (e.g., already having been corrected) and in the current partial image data set. An instant may be chosen as the end of the inflow interval at which the instant may be assumed that no more additional filling occurs, and an instant may be chosen as the beginning of the outflow interval at which the instant may be assumed that emptying starts from this instant or thereafter. It is also conceivable to generate two four-dimensional angiography data sets (e.g., one displays the inflow and one the outflow), with one the partial image data set progressed through forwards in time and another for backwards in time.

With the consideration of outflow intervals, care may be taken during initialization. In other words, when considering the first (e.g., and therefore last) partial image data set that contrast medium has been left behind in vessels is completely pathologically conceivable, contrast medium accumulations without edge reference, remote from the edge, that already exist even in the last partial image data set of the angiography data set, are also regarded as admissible source points. At least one admissible source point may be defined here, and is comparable to a contrast medium administering instrument arranged inside the recording region during inflow.

Artifacts that may occur as early as during normal 3D reconstruction of a vascular tree are sometimes also given as interruption artifacts (e.g., short pieces of individual blood vessels may be absent in the reconstructed three-dimensional vessel data set and therefore in the four-dimensional angiography data set). If it is possible to categorize these interruptions as at least most probably given interruption artifacts (e.g., easily solved mathematically), the contrast medium flow downstream of such an interruption may also be continued by an additional definition as a supplement to a contrast medium-filled connection and/or admissible source points. Therefore, for example, a categorization of interruption regions where an interruption artifact exists may be made, and interruption regions of adjacent voxels (e.g., only in the flow direction of the contrast medium) may be determined as additional admissible source points, and optionally also caused by contrast medium filling on the other side of the interruption given by the possible interruption artifact. Because the vessel data set may be evaluated more accurately for this kind of categorization of interruption artifacts, and because interruption artifacts may be difficult to detect anyway, the present embodiments provide that an interruption to the connection path that satisfies an artifact criterion is also regarded as a contrast medium-filled connection. The artifact criterion may use a temporal connection between filling on either side of the interruption and/or an evaluation result of the vessel data set that points to a vessel section missing due to an interruption artifact and/or a threshold value for a maximum length of the interruption. Further admissible source points may also be comparably defined. There are therefore different methods conceivable for dealing with interruption artifacts, and it may be preferred to risk the assumption that with contrast medium filling on one side of the interruption (e.g., subsequent contrast medium filling separated from the other contrast medium filling by the interruption) may be regarded as an indication of an interruption artifact possibly being present and therefore to continue to leave the vessel section separated by the interruption as being filled with contrast medium in the partial image data set.

The interruption artifact itself is expediently not removed by image processing in order to leave the decision as to whether an interruption artifact actually exists here (e.g., or even whether a pathology may exist here) to the doctor.

An embodiment provides that an algorithm of graph theory for finding connected components is used for determining the vessel sections. As has already been described, the plausibility check is ultimately based on connected components evaluated (e.g., independently of each other as to whether they contain an admissible source point), therefore each contrast medium-filled voxel of a connected component has a connection to an admissible source point. Algorithms for finding connected components may be implemented with minimal mathematical effort and are basically known in the prior art.

In an embodiment, a binary data set is provided displaying the position of the vessel sections that satisfy the plausibility check criterion (e.g., determined by removing vessel sections that do not satisfy the plausibility check criterion in a binary work data set). The binary data set is applied as a mask to the temporally assigned partial image data set or the vessel data set or the base data set. If a binary work data set is worked on as early as in the plausibility check step, the data set and voxels displayed as being filled with contrast medium are distinguished from voxels displayed as not being filled with contrast medium. Algorithms of graph theory that find connected components may be applied easily to binary data sets, resulting in a solution that is easy to implement. The result, when vessel sections that do not satisfy the plausibility check criterion (e.g., voxels in the work data set) are removed (e.g., marked as not contrast medium-filled) is a mask allowing for a new, corrected partial image data set to be cut out for the instant the binary data set refers, of a corresponding source data set. The source data set may be the original (or optionally pre-corrected) temporally assigned partial image data set. However, the mask may be applied to the vessel data set or the base data set derived therefrom (e.g., now containing only image values above a particular threshold value because it has been found that this results in an overall improved and more agreeable display for an observer). A binary data set is determined for each instant or uncorrected partial image data set.

In an embodiment, it may be provided that before the plausibility check act, an interpolation act is performed based on a four-dimensional confidence data set, which as confidence values contains measures determined from the vessel data set for blood vessels located along a beam of the back projection when determining the value of a voxel of a partial image data set, less reliable values in the partial image data sets are replaced by correction values interpolated temporally (e.g., linearly) from more reliable values. In addition to the plausibility check, the confidence methods described above may have already been used in advance to further reduce artifacts. For example, it is ultimately counted how many vessels are located along a beam considered in multiplicative back projection in order to enable a lower confidence value to be assigned in the case of a larger assumed number of vessels and a temporal interpolation in regions relating to lower confidence values. In this way, two correction mechanisms are easily implemented for reducing overlap artifacts and are ultimately combined (e.g., two pathologies) and continue to keep the corrections recognizable.

It is also conceivable to perform a correction or identification of overlap artifacts by considering further hemodynamic properties and/or physical models with respect to conventional flow directions, blood flow speeds, blood properties and the like, which may be less preferred for several reasons. Firstly, the consideration assumes a much more accurate evaluation of the vessel data set because the exact structure of the blood vessels in the recording region of interest must be known in order to apply these models and properties. Secondly, pathologies found in the four-dimensional angiography data set are characterized precisely by the fact that such assumptions about the hemodynamics and other flow properties no longer apply (e.g., such that there is a risk of erroneously removing pathologies as artifacts and removing pathologies from display). The method described is based on a simple physical assumption (e.g., namely the contrast medium may only be where an expedient source connects) and does not use further assumptions of this kind and respects and retains displaying of pathologies thereby.

In addition to the disclosed method, the present embodiments also provide for an image processing device. The device includes a determining unit for determining a four-dimensional angiography data set, recorded with the administration of contrast medium, of a recording region of interest of a blood vessel system of a patient, having a reconstruction sub-unit for reconstruction of a three-dimensional vessel data set of the blood vessel system from two-dimensional projection images from digital subtraction angiography, showing the blood vessel system, and a back projection sub-unit for determining the angiography data set by multiplicative back projection of the projection images into the vessel data set or a base data set derived therefrom. The device also includes a plausibility check unit for checking vessel sections displayed as filled with contrast medium by way of a plausibility check criterion that checks for the existence of a contrast medium-filled connection to an admissible source point in partial image data sets of the angiography data set assigned to all individual, different instants of the covered period. The device further includes a correction unit for determining corrected partial image data sets that now contain only vessel sections that satisfy the plausibility check criterion.

All statements in respect of the method disclosed may be transferred analogously to the disclosed image processing device such that the advantages already known may also be obtained with the device. The image processing device may be implemented as part of an angiography device (e.g., an angiography device having a C-arm). The different units and subunits may be implemented by appropriate software and/or hardware components.

A computer program may be loaded directly into a storage device of an image processing device and having programming configured to carry out the acts of the method described above when the computer program is run in the image processing device. The computer program may be stored on an electronically readable data carrier that includes electronically readable control information stored thereon including at least one said computer program and configured such that the computer program may carry out a method described above when the data carrier is used in an image processing device. The electronically readable data carrier may be a non-transient data carrier (e.g., a CD ROM).

BRIEF DESCRIPTION OF THE DRAWINGS

FIG. 6 shows an exemplary embodiment of an angiography device.

DETAILED DESCRIPTION

Figure 1:
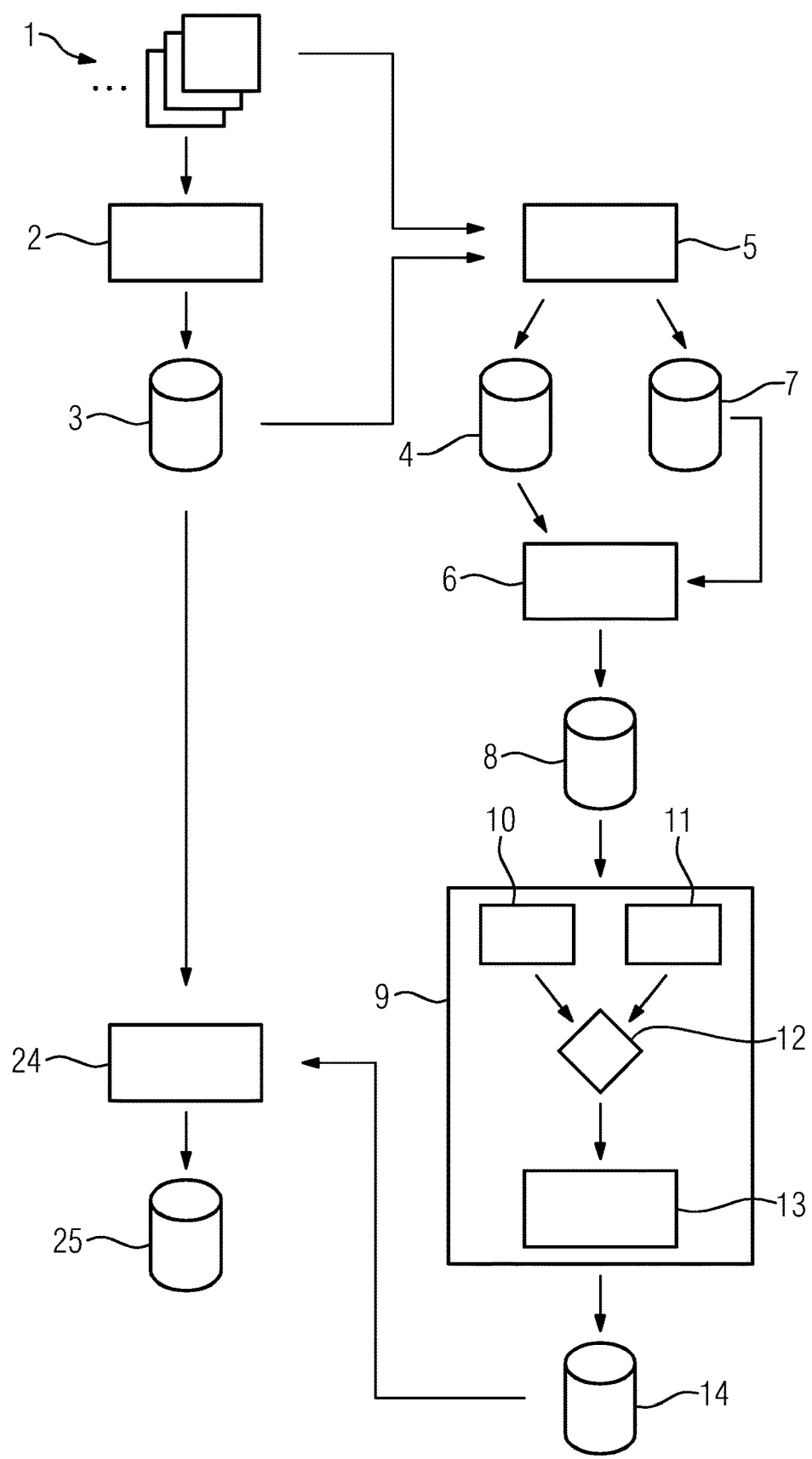
FIG. 1 shows a flowchart of an exemplary embodiment of the disclosed method.

FIG. 1 shows a flowchart of an exemplary embodiment of a method for reducing artifacts. The starting point may be two-dimensional projection images 1 from digital subtraction angiography (e.g., recorded from different directions of projection). For example, using an angiography device having a C-arm during a plurality of revolutions, and in order to obtain the projection images 1 from digital subtraction angiography, a mask image recorded from the respective direction without contrast medium is subtracted. Alternatively, a three-dimensional, reconstructed mask image data set may be subtracted after a reconstruction.

The projection images 1 show a recording area of interest of a vascular tree of a patient and a chronological sequence of the spread of a contrast medium bolus administered in the recording region of interest. It is known to use a rather long contrast medium administration (e.g., 7 seconds) in order to obtain a relatively large number of two-dimensional projection images 1 with an almost completely filled blood vessel system of the patient in the recording region of interest. The corresponding portion of the projection images 1 is used in act 2 to conventionally reconstruct an optimally high-quality, three-dimensional vessel data set 3 that shows the blood vessel system in the recording region completely.

To obtain a provisional four-dimensional angiography data set 4 (e.g., yet to be corrected) in act 5, the projection images relating to the respective instants of the period (e.g., covered by the series of projection images 1) are multiplicatively back-projected in the vessel data set 3 or a base data set derived herefrom (e.g., by using a threshold value, with all vessel data (image values) below the threshold value being cut). Thus, a check is made as to which blood vessels are located along a beam leading to a pixel of the projection image 1 currently being considered. Contrast medium filling of the pixel is then ultimately distributed among the vessel voxels of the vessel data set 3 located on the beam. The multiplication highlights vessel voxels of pixels of the projection image 1 that display contrast medium filling and suppresses vessel voxels pixels without contrast medium filling.

Vessel sections of a blood vessel that overlap a contrast medium-filled blood vessel, but are not yet filled with contrast medium, are highlighted. Thus, the provisional four-dimensional angiography data set 4 may include overlap artifacts.

In the exemplary embodiment of a method as illustrated, a first correction of such overlaps is optionally performed in an interpolation act 6. In preparation for act 6, a four-dimensional confidence data set 7 is determined in act 5. For each voxel and each instant, the confidence data set 7 contains a confidence value as a measure of the reliability of the corresponding angiography data value of the provisional angiography data set 4. To determine the confidence value, a check is performed to determine how many vessel voxels and/or vessels are located along a beam during multiplicative back projection, such that the confidence value ultimately indicates a probability that different blood vessels are located along this beam 2. The confidence value is standardized to an interval between 0 and 1. A confidence value of 1 indicates a high degree of certainty that a plurality of blood vessels is located along the beam; a confidence value of 0 indicates a high degree of certainty that a plurality of vessels is located along the beam.

The angiography data set 4 is ultimately determined as a series of three-dimensional partial image data sets assigned to different instants within the covered period. If individual three-dimensional voxels are considered over the different partial image data sets, a temporal contrast medium characteristic curve results for these voxels. The correction performed in interpolation act 6 is provided such that, due to the directions of projection, which change over time, during recording of the projection images 1, an overlap, and therefore a low reliability, is depicted by a low confidence value, which exists only over certain periods. If less reliable values in successive partial image data sets of the angiography data set 4 are replaced by interpolated values determined by interpolation between reliable, temporally neighboring values in the angiography data set, corresponding contrast medium filling results with a consistent contrast medium curve over time, whereas with reliable values of zero as neighboring values, erroneous contrast medium fillings are removed by the temporal interpolation.

The four-dimensional angiography data set 8 is pre-corrected in this way and is then processed further in a plausibility check act 9 to find physically implausible filling events in the partial image data sets of the pre-corrected angiography data set 8 assigned to individual, particular instants. In an example following only the filling (e.g., inflow of the contrast medium), voxels are highlighted once in the angiography data set 4, 8 and continue to be shown thereafter as filled with contrast medium. Examples following the issuing (e.g., the outflow) of the contrast medium may also be considered (e.g., discussed in more detail below). In the example of a filling series of partial image data sets, the partial image data sets are processed one after the other (e.g., the process is begun with the starting time of the period and each partial image data set is continuously examined one after the other for implausible contrast medium-filled vessel sections until the end time of the period). In plausibility check act 9, connected, contrast medium-filled components existing in the partial image data sets are found with an appropriate algorithm of graph theory (e.g., in sub-act 10). In addition, admissible source points for the instant currently being considered are defined in sub-act 11. The plausibility check criterion checked in sub-act 12 then checks whether voxels displayed as filled with contrast medium of the partial image data set currently being considered are connected to a voxel corresponding to an admissible source point on a contrast medium-filled connection path. Because of the preparation in act 10, a check is easily made as to whether (e.g., in relation to an individual, independently considered, connected component) this component includes an admissible source point. Contrast medium-filled vessel sections that satisfy the plausibility check criterion (e.g., depicted by connected components) are retained in a sub-act 13. Vessel sections displayed as filled with contrast medium, but that do not satisfy the plausibility check criterion, are removed in sub-act 13. A binary work data set is worked with within the plausibility check act 9, simplifying discovery of the connected components significantly. Binarization is performed based on a threshold value. The result of sub-act 13 is a set of binary data sets 14 for each partial image data set, and may be interpreted as a mask, showing where plausible contrast medium-filled vessel sections are located.

Figure 2:
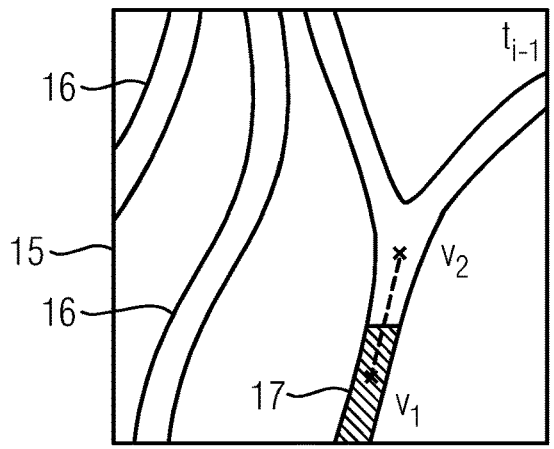
FIG. 2 shows a diagram to illustrate the plausibility check according to an embodiment.
Figure 2:
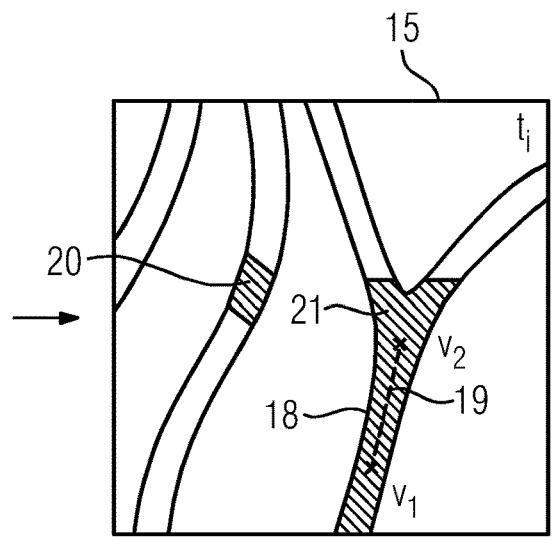
Figure 3:
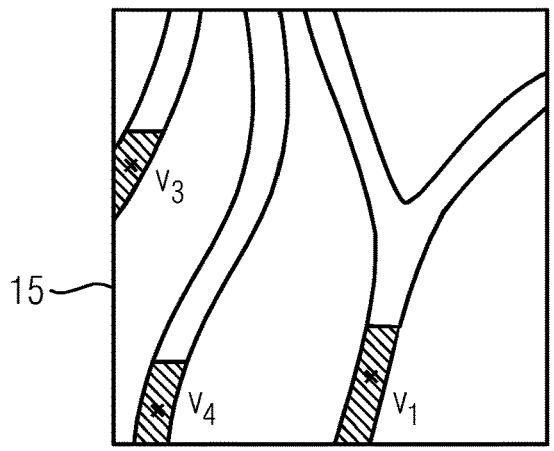
FIG. 3 shows a first diagram relating to the choice of admissible source points according to an embodiment.
Figure 4:
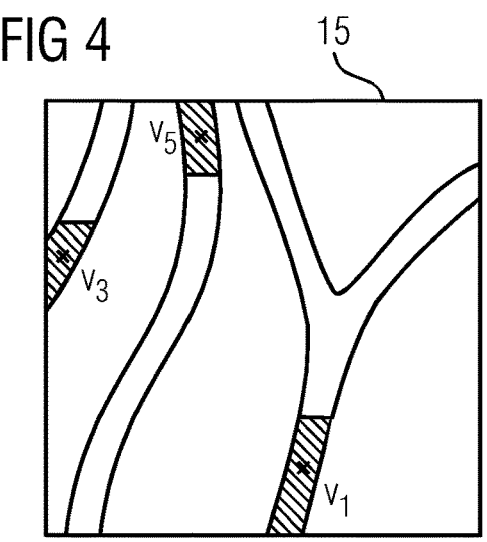
FIG. 4 shows a second diagram relating to the choice of admissible source points according to an embodiment.

The plausibility check performed in sub-act 12 and choice of admissible source points performed in sub-act 11 is illustrated in more detail in FIGS. 2 to 4. FIG. 2 shows second schematically indicated voxels $v_1$ and $v_2$ in the indicated recording region 15 of interest at instant $t_{i-1}$ (left) and at instant $t_i$ (right). The instants $t_{i-1}$ and $t_i$ follow each other in the period. In addition to vessels 16, image information 17 of the partial image data set at instant $t_{i-1}$ and image information 18 of the partial image data set at instant $t_i$ may be seen, indicating where contrast medium exists. For example, the voxel $v_1$ may be an edge voxel of the recording region 15. It is evident in the image information 17 about voxels of the partial image data set that are to be displayed as filled with contrast medium at instant $t_i$, that the voxel $v_2$ should not yet be displayed as filled with contrast medium, and that at instant $t_i$, from image information 18, that the voxel $v_2$ should be displayed as filled with contrast medium. If voxels $v_1$ and $v_2$ are considered, as well as the image information 18 at instant $t_i$, a contrast medium-filled connection 19 may be seen between the voxels $v_1$ and $v_2$ because it is physically plausible for the contrast medium displayed at instant $t_{i-1}$ (e.g., in the case of voxel $v_1$) to have spread to voxel $v_2$, such that the voxel $v_1$ may be understood as an admissible source point for the voxel $v_2$ displayed as filled with contrast medium newly added in the image information 18 at instant $t_i$. The plausibility check criterion in sub-act 12 therefore establishes that the voxel $v_2$ in the partial image data set at instant $t_i$ is only displayed as contrast-enhanced if the voxel $v_1$ identified as an admissible source point exists at instant $t_{i-1}$ and is contrast medium-enhanced and connected.

If, because of a vessel overlap, a vessel section 20 appears in the image information 18 at instant $t_i$, it is not possible to establish a connection to the admissible source point, voxel $v_1$, herefrom, so that filling in the vessel section 20 and therefore the contrast medium-enhanced display of corresponding voxels would be implausible. The plausibility check criterion would not be satisfied there.

Because (e.g., in the first partial image data set or in the first partial image data set in which contrast medium may be seen in the recording region 15) no preceding image information yet exists that may define admissible source points, it is assumed that because the period conventionally covers the surge in the recording region 15, the contrast medium always penetrates into the (e.g., three-dimensional) recording region 15 from the outside. Therefore, voxels located at the edge of the recording region 15 may be understood as an admissible source point. For example, FIGS. 3 and 4 illustrate this by showing such edge voxels $v_1$, $v_3$, $v_4$ and $v_5$. If contrast medium is specified by the image information of the respective partial image data set at these edge voxels, plausibility is basically assumed.

Edge voxels at edge of the recording region 15 may be consistently interpreted as admissible source points in order to be able to also detect a subsequent inflow.

According to FIG. 2, further admissible source points are produced because they may be displayed as filled with contrast medium in the (e.g., corrected) partial image data set of the immediately preceding instant $t_{i-1}$ as well as at the instant $t_i$ currently being considered. The voxel $v_1$ would also be an admissible source point for the instant $t_i$ if it was not an edge voxel and was established as being plausibly filled at instant $t_{i-1}$.

As evident from FIG. 2, two connected components would be established in the right-hand partial image (e.g., namely vessel section 20 and vessel section 21). It may be established that the connection 19 to an admissible source point exists for all voxels of a vessel section 20, 21 if the corresponding connected component contains an admissible source point.

An initial admissible source point may be determined using a position of a contrast medium administering device if the device is located inside the recording region 15.

Figure 5:
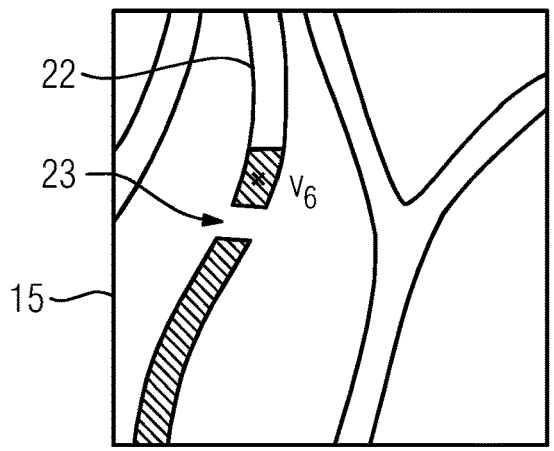
FIG. 5 shows a third diagram relating to the choice of admissible source points according to an embodiment.

FIG. 5 illustrates an optional extension of the plausibility check criterion or the admissible source points. FIG. 5 shows that, in a blood vessel 22, an interruption 23 exists appearing to be an image artifact. With such interruptions 23 assumed by an artifact criterion to be an interruption artifact, successively occurring filling (e.g., as a function of an existing filling on one side of the interruption 23) on the other side may be regarded as admissible either in the neighboring voxels situated in the vessel 22 on the side of the interruption 23 located in the flow direction, or are regarded as admissible source points (e.g., compare the voxel $v_6$ shown). Due to the artifact criterion, it is also conceivable to decide that, despite the interruption 23, a contrast medium-filled, closed connection to an admissible source point exists. The interruption 23 is purposefully not filled here, so that a doctor may decide whether an interruption artifact actually exists, or that an anatomical condition is responsible.

Referring back to FIG. 1, the resulting binary data sets 14 are applied as a mask in act 24 to the vessel data set 3 or the base data set derived herefrom because a higher quality display may be achieved in this way. In other exemplary embodiments, it is conceivable to apply the corresponding mask to the corresponding partial image data sets of the uncorrected or pre-corrected angiography data set 4, 8. In each embodiment, the result is a corrected four-dimensional angiography data set 25 having fewer overlap artifacts.

If the angiography data set 25 shows the outflow of the contrast mediums from the recording region 15, it may be expedient for at least some of the partial image data sets to use the plausibility check criterion in reverse (e.g., starting from the end time of the period). Admissible source points are then determined as voxels displayed as filled with contrast medium that are not located at the edge or connected thereto in order to not accidentally remove pathologies that actually exist (e.g., in which contrast medium as it were "sticks") based on the plausibility check criterion. Pure outflow data sets and the like are also conceivable, which may then expediently be dealt with in plausibility check act 9 in reverse from the end of the period.

FIG. 6 schematically shows an angiography device 26 that may be used in the context of the disclosed method. In addition to a C-arm 27, on which an X-ray emitter 28 and an X-ray detector 29 are opposingly arranged and with which the projection images 1 may be recorded, as well as an associated control unit 30 for controlling the recording operation, in the present embodiments the angiography device 26 includes an image processing device 31 that may also be implemented separately and is configured for carrying out the disclosed method.

For this purpose, the image processing device 31 has a determining unit 32 for determining the provisional angiography data set 4 (e.g., which accordingly has a reconstruction sub-unit 33 and a back projection sub-unit 34). Furthermore, in the present embodiment, an optional interpolation unit 35 is provided for carrying out act 6. For carrying out act 9, a plausibility check unit 36 is provided, and for carrying out act 24, a correction unit 37 is provided. A display unit (not shown) is also conceivable, such as to reproduce views of the resulting four-dimensional, corrected angiography data set 25 on a display device 38.

Although the invention has been illustrated and described in detail by the exemplary embodiments, the invention is not limited by the disclosed examples and a person skilled in the art may derive other variations from the present disclosure without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for reducing vessel overlap artifacts in a four-dimensional angiography data set of a recording region of interest of a blood vessel system of a patient recorded with administration of a contrast medium, wherein a three-dimensional vessel data set of the blood vessel system is reconstructed from two-dimensional projection images from digital subtraction angiography showing the blood vessel system and determined by multiplicative back projection of the projection images into the three-dimensional vessel data set or into a base data set of the four-dimensional angiography data set derived from the three-dimensional vessel data set, the method comprising:
performing, by an imaging processing device, a plausibility check comprising:
checking vessel sections displayed as filled with the contrast medium in partial image data sets of the angiography data set assigned to individual, different instants of a covered period against a plausibility check criterion for an existence of a contrast medium-filled connection to an admissible source point; and
determining a corrected partial image data set with vessel sections that satisfy the plausibility check criterion,
wherein admissible source points are determined as: voxels located at an edge of the recording region, voxels in an immediately preceding partial image data set that have already been corrected and voxels displayed as filled with the contrast medium in a current partial image data set, or a position of a contrast medium administering device inside the recording region.

2. The method of claim 1, wherein an interruption to the connection path satisfying an artifact criterion is regarded as the contrast medium-filled connection.

3. The method of claim 2, wherein the artifact criterion uses a temporal correlation between filling on either side of the interruption, an evaluation result of the three-dimensional vessel data set pointing toward a vessel part missing due to an interruption artifact, or a threshold value for a maximum length of the interruption.

4. The method of claim 1, wherein an algorithm of graph theory for finding connected components is used for determining the vessel sections.

5. The method of claim 1, wherein a binary data set showing a position of the vessel sections satisfying the plausibility check criterion is determined by removing vessel sections that do not satisfy the plausibility check criterion in a binary work data set applied as a mask to the temporally assigned partial image data set, the three-dimensional vessel data set, or the base data set.

6. The method of claim 1, further comprising:
interpolating, prior to performing the plausibility check and based on a standardized four-dimensional confidence data set of measurements determined from the three-dimensional vessel data set for blood vessels located along a beam of the back projection during determination of a value of a voxel of a partial image data set, to replace reliable values in the partial image data sets with correction values interpolated temporally and linearly from more reliable values.

7. An angiography device comprising:
an image processing device configured to:
determine a four-dimensional angiography data set of a recording region of interest of a blood vessel system of a patient recorded with an administration of a contrast medium, wherein a three-dimensional vessel data set of the blood vessel system is configured to be reconstructed from two-dimensional projection images from digital subtraction angiography showing the blood vessel system, and the angiography data set is configured to be determined by multiplicative back projection of the projection images into the three-dimensional vessel data set or a base data set derived from the three-dimensional vessel data set;
check vessel sections displayed as filled with the contrast medium by a plausibility check criterion that checks for an existence of a contrast medium-filled connection to an admissible source point in partial image data sets of the angiography data set assigned to individual and different instants of a covered period; and
determine corrected partial image data sets containing only vessel sections satisfying the plausibility check criterion as a corrected angiography data set,
wherein admissible source points are determined as: voxels located at an edge of the recording region, voxels in an immediately preceding partial image data set that have already been corrected and voxels displayed as filled with contrast medium in a current partial image data set, or a position of a contrast medium administering device inside the recording region.

8. A computer program stored on a non-transitory computer readable medium that when executed on an image processing device, is configured to cause the image processing device to:
reconstruct a three-dimensional vessel data set of a blood vessel system of a patient recorded with an administration of a contrast medium from two-dimensional projection images from digital subtraction angiography showing the blood vessel system and determined by multiplicative back projection of the projection images into the three-dimensional vessel data set or into a base data set of a four-dimensional angiography data set derived from the three-dimensional vessel data set; and
perform a plausibility check comprising:
checking vessel sections displayed as filled with the contrast medium in partial image data sets of the angiography data set assigned to individual, different instants of a covered period against a plausibility check criterion for an existence of a contrast medium-filled connection to an admissible source point; and
determining a corrected partial image data set with vessel sections that satisfy the plausibility check criterion,
wherein admissible source points are determined as: voxels located at an edge of the recording region, voxels in an immediately preceding partial image data set that have already been corrected and voxels displayed as filled with the contrast medium in a current partial image data set, or a position of a contrast medium administering device inside the recording region.

9. The computer program of claim 8, wherein an interruption to the connection path satisfying an artifact criterion is regarded as the contrast medium-filled connection.

10. The computer program of claim 9, wherein the artifact criterion uses a temporal correlation between filling on either side of the interruption, an evaluation result of the three-dimensional vessel data set pointing toward a vessel part missing due to an interruption artifact, or a threshold value for a maximum length of the interruption.

11. The computer program of claim 8, wherein an algorithm of graph theory for finding connected components is used for determining the vessel sections.

12. The computer program of claim 8, wherein a binary data set showing a position of the vessel sections satisfying the plausibility check criterion is determined by removing vessel sections that do not satisfy the plausibility check criterion in a binary work data set applied as a mask to the temporally assigned partial image data set, the three-dimensional vessel data set, or the base data set.

13. The computer program of claim 8, further comprising:
interpolating, prior to performing the plausibility check and based on a standardized four-dimensional confidence data set of measurements determined from the three-dimensional vessel data set for blood vessels located along a beam of the back projection during determination of a value of a voxel of a partial image data set, to replace reliable values in the partial image data sets with correction values interpolated temporally and linearly from more reliable values.

14. A non-transitory electronically readable data carrier on which a computer program is stored, the computer program, when executed, is configured to:
reconstruct a three-dimensional vessel data set of a blood vessel system of a patient recorded with an administration of a contrast medium from two-dimensional projection images from digital subtraction angiography showing the blood vessel system and determined by multiplicative back projection of the projection images into the three-dimensional vessel data set or into a base data set of a four-dimensional angiography data set derived from the three-dimensional vessel data set; and
perform a plausibility check comprising:
checking vessel sections displayed as filled with the contrast medium in partial image data sets of the angiography data set assigned to individual, different instants of a covered period against a plausibility check criterion for an existence of a contrast medium-filled connection to an admissible source point; and
determining a corrected partial image data set with vessel sections that satisfy the plausibility check criterion,
wherein admissible source points are determined as: voxels located at an edge of the recording region, voxels in an immediately preceding partial image data set that have already been corrected and voxels displayed as filled with the contrast medium in a current partial image data set, or a position of a contrast medium administering device inside the recording region.

* * * * *